United States Patent
Zingaretti et al.

(10) Patent No.: US 10,327,801 B2
(45) Date of Patent: Jun. 25, 2019

(54) SYSTEMS AND METHODS FOR CREATING HAIR TRANSPLANTATION PROCEDURE SITES

(71) Applicant: Restoration Robotics, Inc., San Jose, CA (US)

(72) Inventors: Gabriele Zingaretti, Capitola, CA (US); Ognjen Petrovic, Mountain View, CA (US)

(73) Assignee: Restoration Robotics, Inc., San Jose, CA (US)

(*) Notice: Subject to any disclaimer, the term of this patent is extended or adjusted under 35 U.S.C. 154(b) by 0 days.

(21) Appl. No.: 16/017,877

(22) Filed: Jun. 25, 2018

(65) Prior Publication Data

US 2018/0310952 A1  Nov. 1, 2018

Related U.S. Application Data

(63) Continuation of application No. 14/448,550, filed on Jul. 31, 2014, now Pat. No. 10,004,530.

(51) Int. Cl.
| | |
|---|---|
| A61B 17/3205 | (2006.01) |
| G06F 17/00 | (2019.01) |
| A61B 34/10 | (2016.01) |
| A61B 34/30 | (2016.01) |
| A61B 17/00 | (2006.01) |
| A61B 90/00 | (2016.01) |

(52) U.S. Cl.
CPC ........ *A61B 17/32053* (2013.01); *A61B 34/10* (2016.02); *A61B 34/30* (2016.02); *A61B 90/06* (2016.02); *A61B 90/361* (2016.02); *A61B 2017/00752* (2013.01); *A61B 2034/107* (2016.02); *A61B 2090/061* (2016.02)

(58) Field of Classification Search
None
See application file for complete search history.

(56) References Cited

U.S. PATENT DOCUMENTS

| | | | |
|---|---|---|---|
| 3,842,439 A | | 10/1974 | Connelly et al. |
| 5,397,327 A | * | 3/1995 | Koop .................. A61B 18/201 606/17 |
| 6,585,746 B2 | | 7/2003 | Gildenberg |
| 7,792,333 B2 | | 9/2010 | Aradhye et al. |
| 7,806,121 B2 | | 10/2010 | Bodduluri |
| 8,115,807 B2 | | 2/2012 | Rassman et al. |

(Continued)

FOREIGN PATENT DOCUMENTS

| | | |
|---|---|---|
| CN | 101277657 A | 10/2008 |
| CN | 102026585 A | 4/2011 |

(Continued)

OTHER PUBLICATIONS

International Search Report, ROC (Taiwan) Pat. Application No. 104120033, dated Apr. 24, 2017.

(Continued)

*Primary Examiner* — Paulinho E Smith

(57) ABSTRACT

Methods and systems are provided for determining the location of procedure sites, for example hair implantation sites, the method and systems enabling a natural looking randomness to be maintained to achieve a desired density while avoiding previously created procedure sites and existing features.

18 Claims, 8 Drawing Sheets

(56) References Cited

U.S. PATENT DOCUMENTS

| | | | |
|---|---|---|---|
| 8,911,453 B2 | 12/2014 | Tenney et al. | |
| 8,945,150 B2 | 2/2015 | Bodduluri et al. | |
| 9,202,312 B1* | 12/2015 | Zingaretti | G06T 19/20 |
| 9,498,289 B2 | 11/2016 | Zhang et al. | |
| 2003/0040766 A1 | 2/2003 | Werner | |
| 2007/0078466 A1 | 4/2007 | Bodduluri et al. | |
| 2007/0106306 A1 | 5/2007 | Bodduluri et al. | |
| 2007/0150247 A1* | 6/2007 | Bodduluri | G16H 50/50 703/11 |
| 2007/0207100 A1 | 9/2007 | Adams | |
| 2008/0167674 A1* | 7/2008 | Bodduluri | A61M 5/20 606/187 |
| 2008/0216334 A1 | 9/2008 | Pak et al. | |
| 2009/0306680 A1 | 12/2009 | Qureshi et al. | |
| 2011/0022371 A1 | 1/2011 | Bodduluri | |
| 2012/0116417 A1 | 5/2012 | Bodduluri et al. | |
| 2012/0179189 A1* | 7/2012 | Zingaretti | G06T 7/0004 606/187 |
| 2012/0296343 A1* | 11/2012 | Bodduluri | A61F 2/10 606/133 |
| 2013/0190776 A1 | 7/2013 | Zhang et al. | |
| 2014/0261467 A1* | 9/2014 | Zhang | A61F 2/10 128/898 |
| 2014/0276092 A1* | 9/2014 | Tenney | A61B 5/1072 600/476 |
| 2014/0278321 A1* | 9/2014 | Zhang | A61B 5/0077 703/11 |
| 2016/0030075 A1* | 2/2016 | Zingaretti | A61B 17/32053 606/187 |
| 2016/0030134 A1* | 2/2016 | Shapter | G06F 3/0488 606/130 |
| 2016/0034652 A1* | 2/2016 | Zingaretti | A61B 34/10 706/11 |
| 2016/0136071 A1 | 5/2016 | Corboy, Jr. | |
| 2016/0148435 A1* | 5/2016 | Li | G06T 19/20 715/835 |
| 2017/0032223 A1* | 2/2017 | Zingaretti | G06T 7/0012 |

FOREIGN PATENT DOCUMENTS

| | | | |
|---|---|---|---|
| CN | 103260550 A | | 8/2013 |
| JP | 2015061614 A | * | 4/2015 ........... G06T 7/0004 |
| JP | 2015061614 A | | 4/2015 |
| WO | 2012087929 A2 | | 6/2012 |
| WO | 2012094637 A2 | | 7/2012 |
| WO | 2016019203 A1 | | 2/2016 |
| WO | WO-2016019203 A1 | * | 2/2016 ....... A61B 17/32053 |

OTHER PUBLICATIONS

European Search Report, 15828113, dated Jul. 21, 2017.

English Translation of Office Action dated Jan. 10, 2017, in connection with commonly assigned Taiwanese Patent Application No. 104120033, (2 pages).

PCT International Search Report and Written Opinion, in connection with commonly assigned PCT International Application No. PCT/US2015/043021, dated Nov. 2, 2015, (13 pages).

Alhaddab, et al., "Effect of Graft Size, Angle, and Intergraft Distance on Dense Packing in Hair Transplant", Dermatol Surg. 31:6, Jun. 2005, 650-654.

Bernstein, et al., "Follicular Transplantation", International Journal of Aesthetic and Restorative Surgery. vol. 3, No. 2., 1995, 119-132.

Bernstein, et al., "The Logic of Follicular Unit Transplantation", Dermatologic Clinics vol. 17, No. 2,, Apr. 1999, 277-296.

Gibbons, et al., "Quantification of Scalp Hair—A Computer-Aided Methodology", The Society for Investigative Dermatology, Inc. vol. 86. No. 1, Jan. 1986, 78-82.

Jimenez, et al., "Distribution of Human Hair in Follicluar Units—A Mathematical Model for Estimating the Donor Size in Follicular Unit Transplantation", Dermatol Surg. 25:4, Apr. 1999, 294-298.

Rassman, et al., "Micrografting in Extensive Quantities", http://www.newhair.com/resources/mp-1995-micrografting.asp, (7 pages).

Shapiro, "Principles and techniques used to create a natural hairline in surgical hair restoration", Facial Plast Surg Clin N Am 12 (2004), 2004, pp. 201-217.

Avram et al.; "The Use of Low Level Light for Hair Growth: Part 1", 2009 Journal of Cosmetic and Laser Therapy, vol. 11, pp. 110-117.

English Translation of Office Action dated Feb. 21, 2017, in connection with commonly assigned Korean Patent Application No. 10-2017-7001305 (2 pages).

* cited by examiner

SYSTEMS AND METHODS FOR CREATING HAIR TRANSPLANTATION PROCEDURE SITES

CROSS-REFERENCE TO RELATED APPLICATIONS

This application is a Continuation of U.S. application Ser. No. 14/448,550, filed Jul. 31, 2014.

TECHNICAL FIELD

The current disclosure relates generally to methods and systems for creating procedure sites. In particular, the current disclosure relates to the creation of implantation sites for hair transplantations.

BACKGROUND

Hair transplantation procedures are well-known, and typically involve (e.g., in a patient having male pattern baldness) harvesting donor hair grafts from the side and back fringe areas ("donor areas") of the patient's scalp, and implanting the harvested follicular units in a bald area ("recipient area"). The donor hair grafts are typically follicular units, which are naturally occurring aggregates of 1-3 (and much less commonly, 4-5) closely spaced hair follicles that are distributed randomly over the surface of the scalp.

While there are various types of the hair transplantation procedures that exist today, no matter what type of hair transplant procedure is adopted, it is the aim of the physician to provide his patient with a natural looking head of hair. Currently, physicians manually create implantation sites, including front hairlines, and do this based on their experience with the procedures performed on prior patients, hoping to do so in such a way that a natural looking head of hair results.

The patient undergoing the hair transplantation treatment is typically expecting to have hair grafts transplanted in such a way that matches his/her existing hair, and nobody can tell that he/she has actually had a hair transplantation procedure performed. New and improved methods for achieving this in automated fashion are needed.

SUMMARY

A variety of systems and methods for substantially automatically determining or selecting the location of procedure sites in cosmetic and dermatological procedures, including hair transplantation, are provided in the present disclosure. These procedures may be performed on the scalp, face and other skin and body surfaces.

According to one aspect of the present disclosure, a method for automatically selecting a location of a procedure site is provided, the method comprising: proposing a candidate procedure site; automatically determining if a location of the candidate procedure site and locations of at least two pre-existing or previously proposed sites positioned within an examination region would represent points on a fitted line and/or form a predefined geometric shape, if such fitted line and/or predefined geometric shape were to be drawn through the locations of the candidate procedure site and the at least two pre-existing or previously proposed sites; and based on the results of the automated determination, either confirming the selected candidate procedure site or automatically modifying the location of the candidate procedure site, such that the modified location of the candidate procedure site and the locations of the at least two pre-existing or previously proposed sites do not represent points on the fitted line and/or form the predefined geometric shape.

In some embodiments, a step of proposing a candidate procedure site may be performed separately and independently, for example, manually by physician or other user, and then the automated system (such as a computing or processing device) may be programmed to perform the remaining steps by confirming the initial selection or by changing it. In those embodiments, the method will start with a step of automatically determining if a location of a candidate procedure site and locations of at least two pre-existing or previously proposed sites positioned within an examination region would represent points of substantially a straight line, a predefined curve segment or a predefined geometric shape, and then continue on as described above.

In some embodiments, automatically modifying the location of the candidate procedure site comprises selecting a new candidate procedure site or adjusting the location of the selected candidate procedure site. In various embodiments offsetting comprises offsetting the location of the candidate procedure site in one or more of a predetermined direction, by a predetermined distance, or a predetermined angle. In some embodiments, representing points that form the predefined geometric shape comprises points located within a band or range of values from vertices of the predefined geometric shape. The fitted line and/or predefined geometric shape may be defined in a 2-D plane or a 3-D environment.

In various embodiments, at least one of the at least two pre-existing or previously proposed sites may comprise a hair graft or hair follicle. In other embodiments, the at least two pre-existing sites may be implantation sites, including those previously proposed or made. The method may additionally comprise determining if the hair graft or hair follicle comprises a terminal hair.

According to a further aspect of the current disclosure, a method of selecting a location of a procedure site is provided. The method comprising: determining locations of at least two pre-existing or previously proposed sites within an examination region; and using a processor to propose a location of a new candidate procedure site such that the proposed location of the new candidate procedure site and the at least two pre-existing or previously proposed sites do not represent points on a fitted line and/or form a predefined geometric shape, if the fitted line and/or the predefined geometric shape were to be drawn through the locations of the candidate procedure site and the at least two pre-existing or previously proposed sites.

According to a yet further aspect of the current disclosure, a method of operating a tool is provided, the method comprising: determining a location of a proposed candidate procedure site and at least two other sites within an examination region; determining if the location of the proposed candidate procedure site and the location of the at least two other sites form a fitted with respect to each other; if the location of the proposed candidate procedure site and the locations of the at least two other sites form the fitted line, adjusting the location of the proposed candidate procedure site such that it does not form the fitted line with the locations of the at least two other sites; and placing a tool at the adjusted location of the proposed procedure site to perform a procedure.

According to a yet further aspect of the current disclosure, a system for selecting a location of a procedure site is provided, the system comprising: a user interface including a user input device; at least one non-transitory storage medium storing instructions, and one or more modules for executing operations on image data, the one or more modules comprising instructions for: determining if a location of a candidate procedure site and locations of at least two pre-existing or previously proposed sites within an examination region would represent points on a fitted line and/or form a predefined geometric shape; and based on the results of the determination, either confirming the selected candidate procedure site or automatically modifying the location of the candidate procedure site, such that the modified location of the candidate procedure site and the locations of the at least two pre-existing or previously proposed sites do not represent points on the fitted line and/or form the predefined geometric shape.

Other features and advantages of the devices and methodology of the present disclosure will become apparent from the following detailed description of one or more implementations when read in view of the accompanying figures. Neither this summary nor the following detailed description purports to define the invention. The invention is defined by the claims.

BRIEF DESCRIPTION OF THE DRAWINGS

It should be noted that the drawings are not to scale and are intended only as an aid in conjunction with the explanations in the following detailed description. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Features and advantages of the embodiments described herein will become appreciated as the same become better understood with reference to the specification, claims, and appended drawings wherein:

DETAILED DESCRIPTION OF THE SPECIFIC EMBODIMENTS

In the following Detailed Description reference is made to the accompanying drawings that show by way of illustration specific embodiments in which the inventions may be practiced. It is to be understood that other embodiments and examples may be utilized and structural or logical changes may be made without departing from the scope of the present disclosure. Also, various features and elements that may be discussed in reference to particular embodiments may be combined together in other embodiments. It should be noted that although the disclosure is particularly useful in medical and/or cosmetic applications, such as for planning hair harvesting, site making, hair implantation or other hair restoration treatments, it is not limited to use for hair transplantation and hair restoration. The disclosure may also be beneficial to other procedures and applications that require a plurality of sites to be created, in a randomized fashion. Such procedures, for example, involving a plurality of injection sites and randomization may benefit from the systems and methods described herein. Some examples of applicability of the disclosure is in medical, cosmetic, plastic-reconstruction or dermatological procedures on a chest, face or other body parts. Procedures such as micropigmentation, a procedure in which an organic pigment is embedded beneath the skin to add permanent color, for example to represent hair stubble, or perhaps permanent makeup. For convenience of description, the following description will be discussed by example in reference to hair transplantation procedures. It should be noted, however, that such description is for the purposes of illustration and example only and is not intended to be exhaustive or limiting.

Figure 1A:
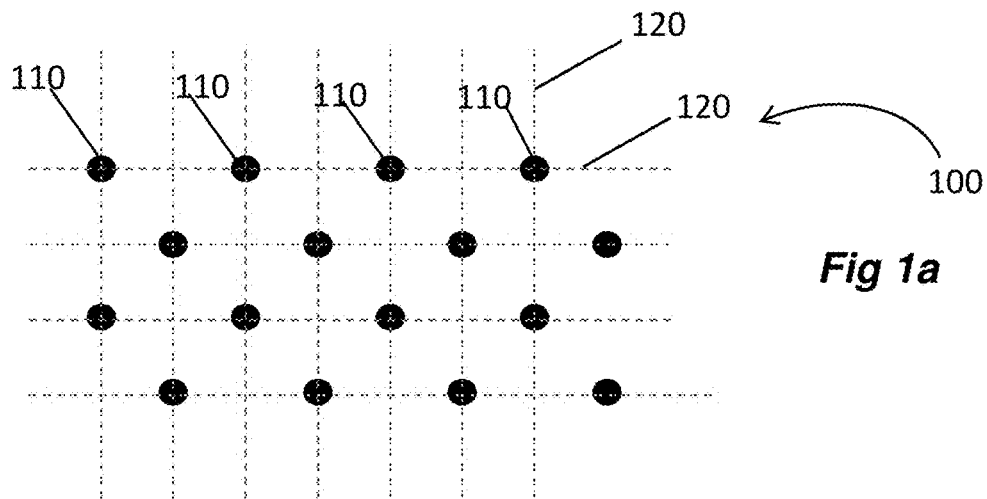
FIGS. 1a and 1b illustrate examples of a uniform distribution of implantation sites within a recipient region without showing any existing hair.
Figure 1B:
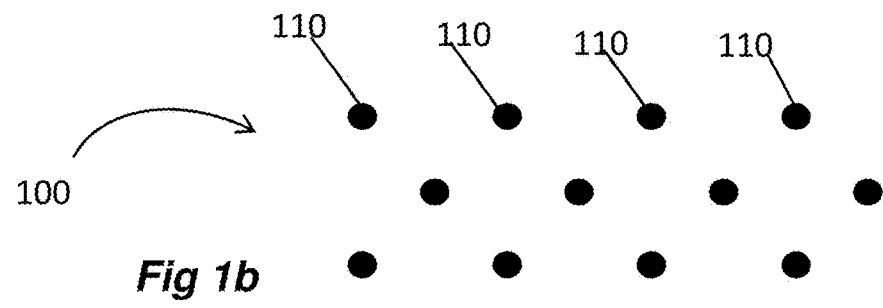

FIG. 1a illustrates one example of the follicular unit implantation sites that might be created utilizing an automated or semi-automated implantation site methodology. In this particular example, assume that the patient is undergoing a procedure in which follicular units are to be implanted into a bald region 100, which is a region where there are no existing follicular units. In addition, assume that the physician has provided input into an automated (or semi-automated) system that a uniform density of follicular unit implantation site be provided within the bald region 100. Since an automated procedure requires instruction as to how to create the implantation sites, in this example, the system has created implantation sites 110 which are uniformly distributed over the bald region 100, at substantially the same distance from each other. To aid in the understanding of how an automated system may achieve this goal, grid lines 120 have been identified as an example. In this example, the automated system may utilize such grid lines 120 to calculate how evenly distribute implantation sites 110 over the required region 100. The result, with the grid lines 120 removed, is illustrated in FIG. 1b. FIG. 1b shows a pattern of implantation sites 110, four rows of implantation sites 110, with four implantation sites 110 in each row. Should follicular unit be implanted into these implantation sites, it will be evident that this will result in an artificially symmetrical and as a result unnatural-looking hair transplant.

Figure 2A:
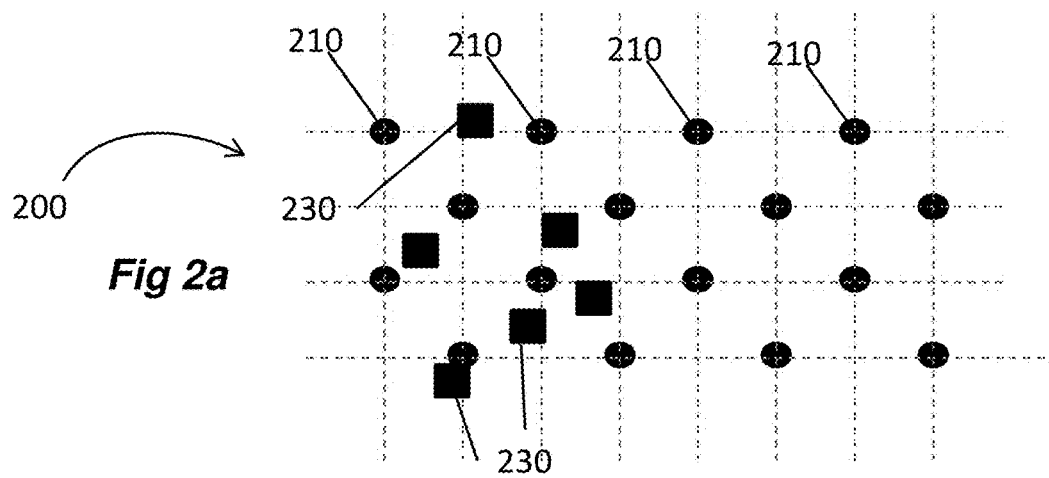
FIGS. 2a and 2b illustrate examples of a uniform distribution of implantation sites within a recipient region, also showing existing hair.
Figure 2B:
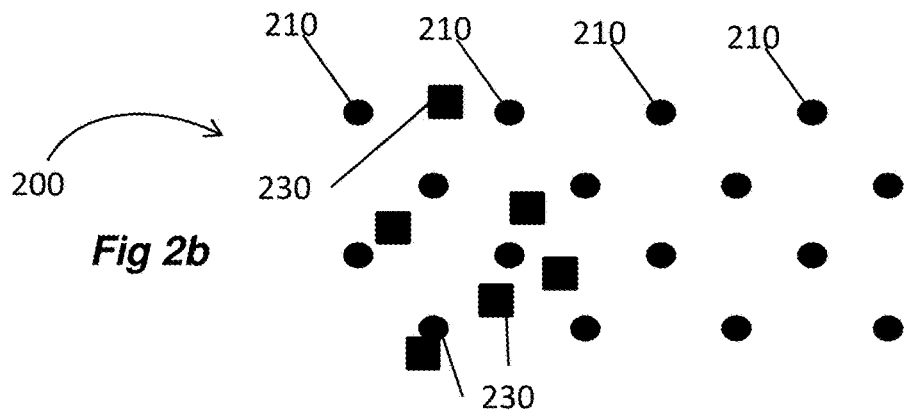

If it is now assumed that the hair transplant patient has some hair 230 in this substantially bald region 200, it can be seen in FIGS. 2a and 2b that if the patient were to have a similar automated hair transplantation procedure performed, a similarly undesirable result would be achieved. In this particular example, the automated system created implantation sites 210 without giving any consideration to the existing follicular units 230 in the substantially bald region 200. As illustrated, on the right hand side of the substantially bald region 200, the implantation sites 210 are evenly distributed creating an artificial looking "doll-like" hair. On the left hand side of the substantially bald region 200, the implantation sites 210 are also evenly distributed, but in some cases are close to, or partially or fully coincide with existing follicular units 230. This not only looks unnatural, but in some cases may create additional issues. For example, the creation of an implantation site which partially or fully coincides with an already existing follicular unit 230 under some circumstances may cause the already existing follicular unit to be destroyed or damaged when the implantation site is created. In the worst case scenario, in addition to the damage to the existing follicular unit, any follicular unit that is subsequently implanted into such new implantation site may not be retained in the patient's scalp. In essence, the patient, would have lost one or more pre-existing hair, and not acquired any "new" hair in that region.

Figure 3A:
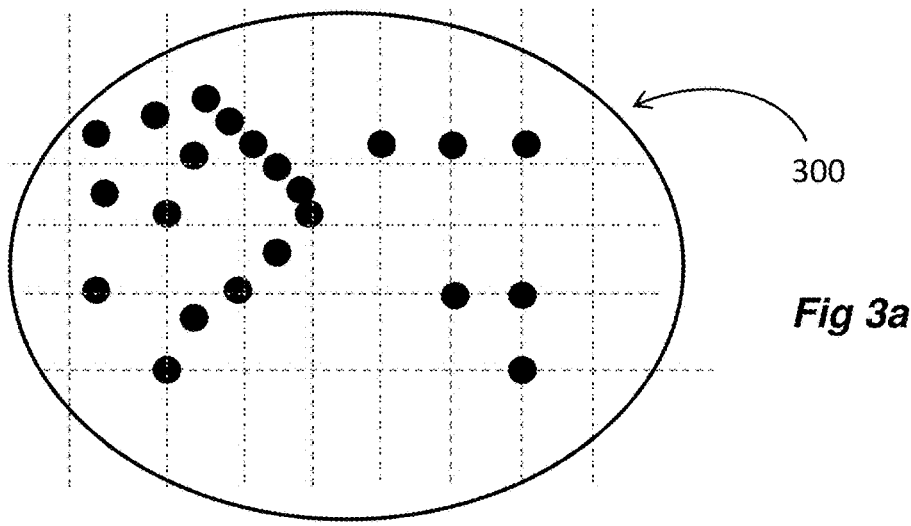
FIGS. 3a and 3b illustrate deficiencies of a purely randomized distribution of implantation sites within a recipient region.
Figure 3B:
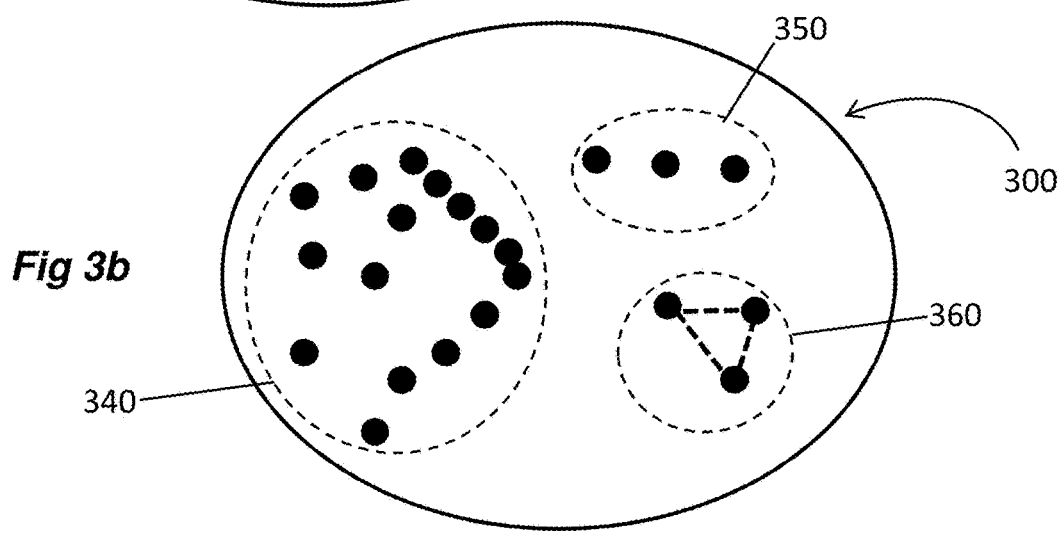

FIGS. 3a and 3b illustrate how randomizing without any restrictions or conditions the location of the implantation sites can similarly result in unnatural-looking hair transplantation. In this example, as with FIGS. 1a and 1b, it is assumed that the patient has a bald region 300, into which he/she desires that hair be evenly distributed. In this particular example however, the methodology applied to the creation of implantation sites has added a randomization factor in the hope of achieving a more natural-looking result. As can be seen, this may not necessarily be the case. FIGS. 3a and 3b illustrate three potential problems, though it will be appreciated that this is only illustrative of the problem, which may result from such randomization. Turning first to the group of implantation sites identified by reference numeral 340, and ignoring the groupings 350 and 360 in this instance, randomization may cause the implantation sites to be created in such a way that they group on one side of the bald region 300. Although the location of the sites has been randomized, and it is apparent that these implantation sites are no longer evenly distributed over the bald region 300, randomization resulted in a dense grouping 340 of implantation sites on one side of the bald region 300, and left the other side bald. In another instance, randomization may cause follicular units or hair grafts, such as those identified by reference numeral 350, to appear to be positioned approximately along the same straight line, and as such provide an unnatural appearance. A further potential problem caused by randomization is illustrated by the implantation sites grouped and referenced by numeral 360. Here the randomization has caused the implantation sites to be positioned approximately on the vertices of an equilateral triangle, and as such form a geometric shape which may look unnatural on the scalp, particularly if this is one of many such triangles or geometric shapes formed. A plurality of such groupings will in fact result in an overly symmetrical implantation site pattern similar to that illustrated in FIGS. 1a and 1b.

The patient undergoing the hair transplantation treatment typically expects receiving a hair transplant in which the hair he/she receives is transplanted in such a way that is matches his/her existing hair, and nobody can tell that he/she has actually had a hair transplantation procedure performed. This typically means that the hair is substantially evenly distributed over the regions in which the hair has been transplanted without creating unnatural symmetrical "doll-like" look. Therefore, one would like to achieve a natural looking somewhat controlled randomness, which is important not only for the critical hairline element but in the balance of the recipient sites too. For these reasons, in a hair transplant procedure it may be desirable to take into account any existing hair on the patient's head, for example, the density or the distribution of existing hair, its spacing, angles, how the patient generally parts and/or combs his hair, or whatever else contributes to making the hair transplant look natural. In addition, one may also take into consideration any other features present on the skin or other body surface that may affect the manner in which hair grafts should be implanted into the patient's recipient areas. Such features may include, but not limited to, for example, moles, freckles, scars, wrinkles, bumps, depressions etc.

The present disclosure provides various solutions for improving a natural looking appearance of the created procedure sites, such as implantation sites. One aspect of the current disclosure enables a natural looking randomness to be maintained in the implanted follicular units throughout the patient's scalp. In another aspect of the current disclosure, the location of procedure sites, for example hair implantation sites, can be automatically planned or created to achieve a desired density while avoiding at least some of the previously created procedure sites and/or existing follicles. It will be appreciated by those skilled in the art that the present disclosure is not limited to the use of a particular system, and that automated (including robotic) or semi-automated apparatus may be used carrying out the methods disclosed herein.

Although the various examples and embodiments described herein will use hair grafts or follicular units (naturally occurring aggregates of 1 to 4 hair follicles) for purposes of describing various aspect, embodiments and implementations, it should be apparent that the general understanding of the various concepts discussed can be applied more broadly to other appropriate applications.

Figure 4A:
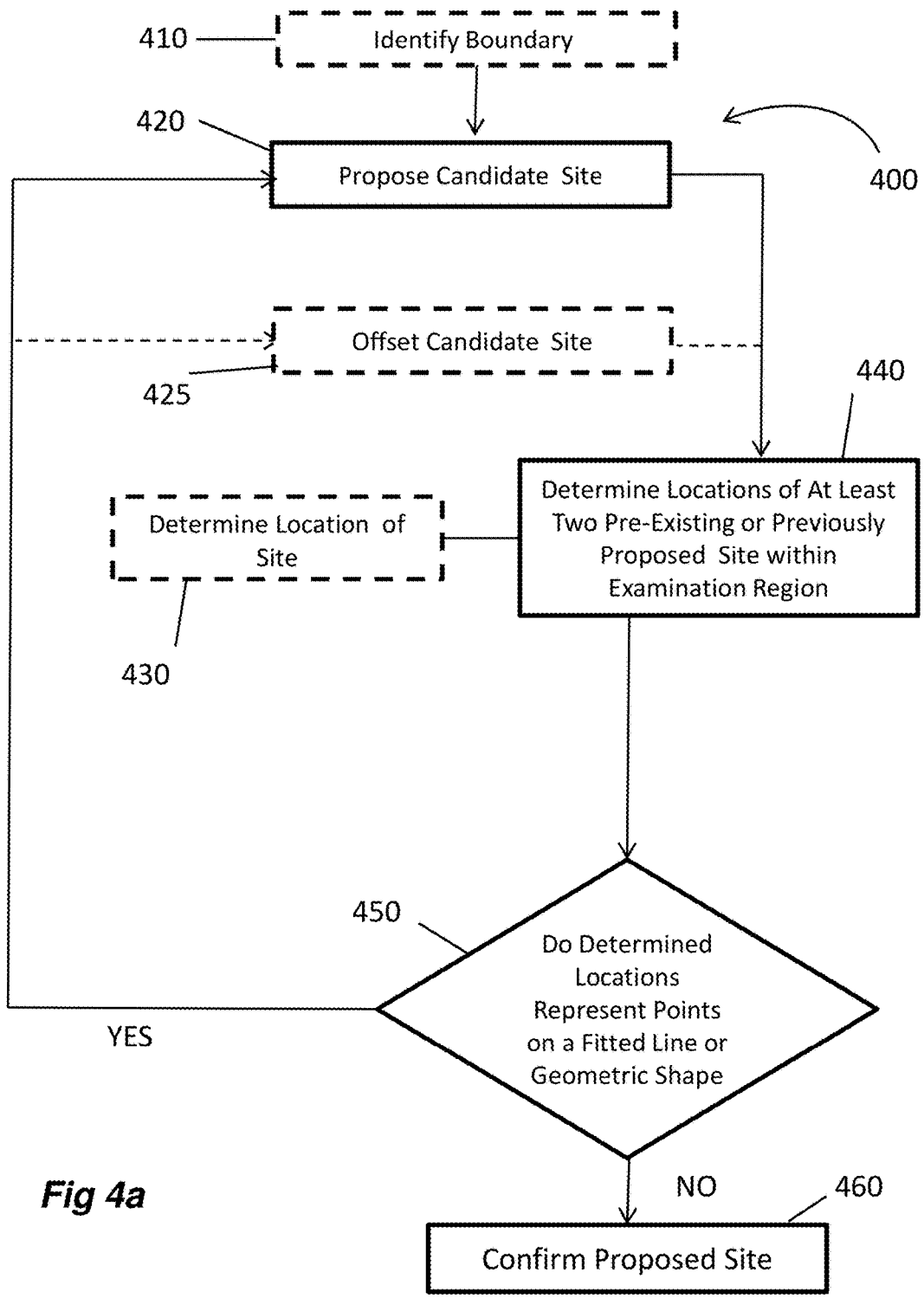
FIG. 4a is a flow chart illustrating an example of a general methodology according to one aspect of the present disclosure.
Figure 6A:
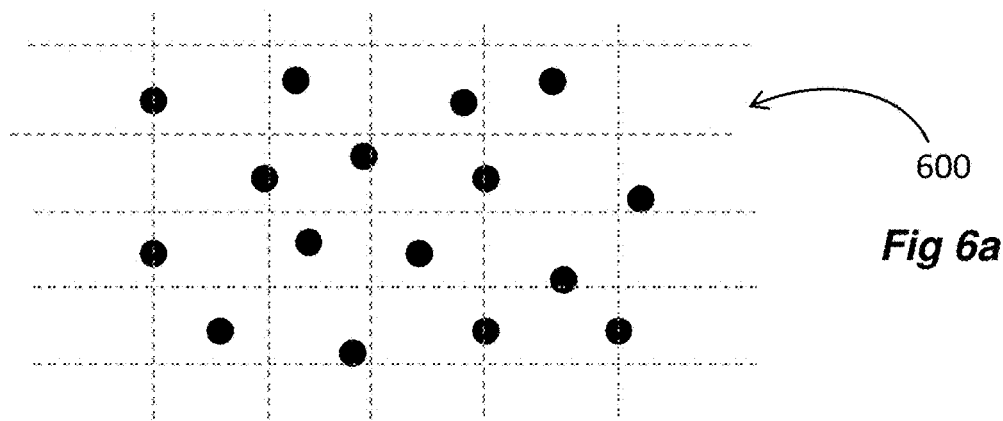
FIGS. 6a and 6b show examples of the possible results from utilizing the general methodology in one embodiment.
Figure 6B:
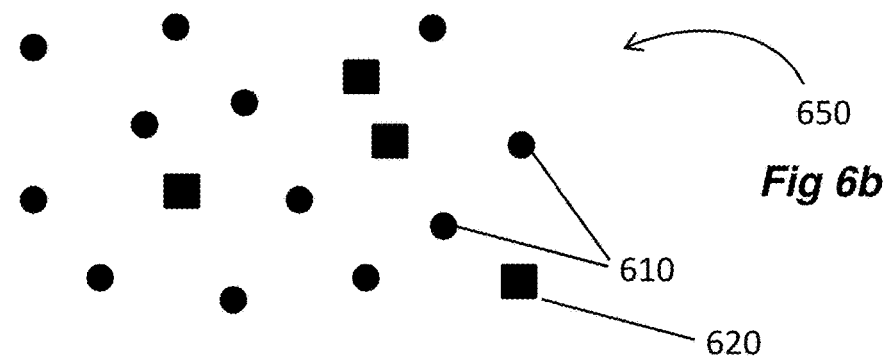
Figure 7:
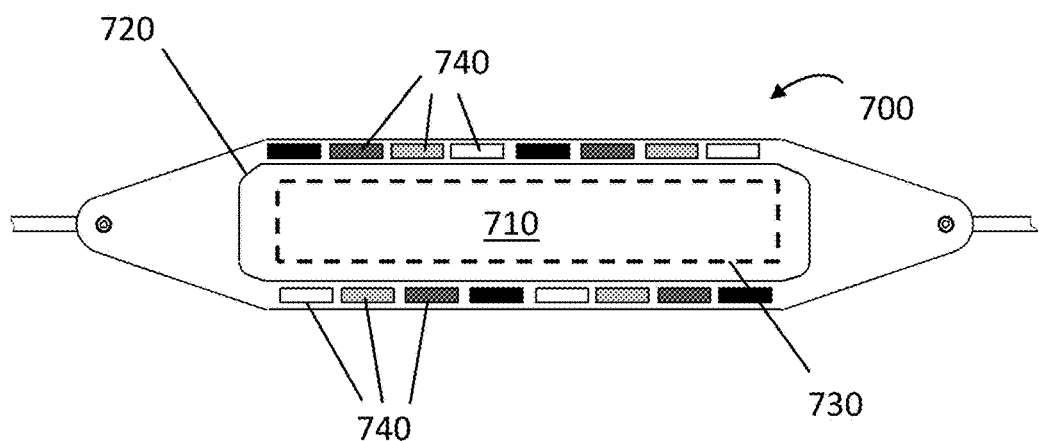
FIG. 7 illustrates an example of a locator device, which may be utilized when implementing methodology of the present disclosure.

FIG. 4a is a flow chart illustrating an example of a general methodology employed by the present disclosure. To assist in the understanding of this flow chart, reference will also be made to FIGS. 5a-5c, 6a-6b, and 7. The proposed methods may be substantially automated, which means that at least most of the steps could be performed automatically, for example, by a processor or other computing device. It does not exclude, however, that the user may intervene and participate, for example, by giving an alternative command through a user interface, or override the automated command. Prior to or as a part of the methodology of the present disclosure, in some implementations a boundary of an area on a body surface where a procedure (e.g., injection site making, or hair implantation site making) is to be performed may be determined, then such determined boundary may be used to plan the proposed locations of the procedure sites. In reference to FIG. 4a, step 410 is shown by dotted line to indicate that this step of identifying boundary is optional or preliminary, and that the boundary may be determined in advance by any means or may not be determined at all. In some implementations where a boundary is determined, information about the determined boundary may be accessed by a processor, which then determines the appropriate locations of the procedure sites within such determined boundary. In one implementation, as shown in FIG. 4a, at step 410, one or more processor or image processor, may process and record the location of a boundary of an area, such as an area within which hair grafts or follicular units are intended to be implanted into. The procedure boundary area may be determined as described in commonly assigned U.S. Patent Application Publication No. US 2013-0190776, which is incorporated herein by reference in its entirety. As described in the above-mentioned application, the boundary may be determined based on a reference, for example, a plurality of fiducials, which may comprise a set of distinctive fiducials. In some embodiments, with reference to hair transplantation, the selection of follicular unit implanting sites may take into account limitations of a tool used in the procedure. Also, the boundary may be adjusted to eliminate portions, for example, where a tool used in the procedure has limited or insufficient access for proper operation, or to take into account one or more additional parameters. According to some embodiments, defining the boundary may be carried out, for example, by using a locator device 700, a device as illustrated in FIG. 7 that could be used in the hair harvesting and/or hair implantation procedure, and which may optionally tension the skin if tensioning is desired. Such a device is described in commonly assigned U.S. Patent Application Publication No. US 2014-0074115. In the illustrated example of FIG. 7, a locator device 700 comprises a central opening 710, bounded by the four side sections of the locator device 700 which define a boundary 720, which could represent an area within which it is desired that follicular units or hair grafts be implanted into. The boundaries 720 and/or 730 may be determined or derived automatically, for example, by drawing lines between various fiducials 740 that may be positioned on the locator device 700. Utilization of such a device, in some embodiments may require other factors be taken into consideration when identifying the actual bound area where follicular units will be implanted. One such factor is that some of the locator devices may be flat and lie flush with the skin, but other locator devices may have a depth or height associated with it, that is, they may not lie flush with the patient's body surface, but may be raised above the body surface to a certain degree. It will also be appreciated that the angle at which the follicular units extend from the patient's body surface varies. To this end, there may be situations in which, due to the depth/height of the locator device 700, the tool that will be placed inside the central opening 710 of the locator device 700 may not be able to be oriented properly relative to the body surface without interfering with the inner edges of the locator device 700 that defines the opening 710. For this reason, one may also take into consideration, for example, a depth or height of the inner edge of the locator device/tensioner when applicable, and/or an angle and dimensions of the procedure tool when it is positioned relative to a desired orientation of the hair graft to be implanted. When these distances, angles and other relevant parameters are taken into account, a revised boundary 730 may result. This revised boundary 730 provides a predetermined distance from the actual physical boundary 720 that the tool may safely approach, without encountering the physical inner boundaries of the locator device 700 itself In some implementations such revised boundary 730 may be substantially automatically determined, for example, by a processor.

Figure 5A:
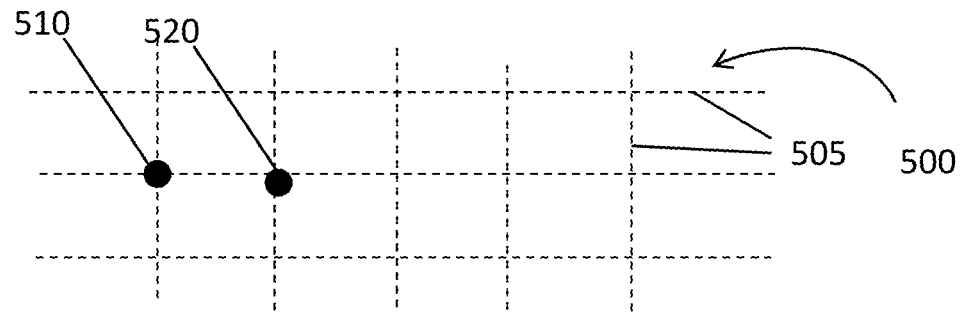
FIGS. 5a-5c show various examples of implementations of the methodology according to an embodiment of the present disclosure.
Figure 9:
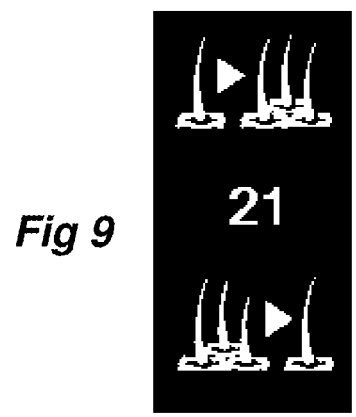
FIG. 9 illustrates an example of a user interface icon, which may be utilized to vary the density within a recipient region.

FIG. 5a illustrates an implantation region 500, comprising a bald region and onto which a grid 505 has been overlaid to aid explanation. The initial first and/or second implantation sites 510 and 520 may be selected within the boundary 720 or 730, for example, by a physician (e.g., manually or by clicking on an image to identify the desired location), or a processor may be configured and programmed to find such sites itself, for example, based on the information it has acquired using fiducials. In some embodiments, the procedure may be performed at the selected procedure site, for example, a site-making tool may be moved to the selected implantation site to make an incision in which a hair graft may be later implanted. In other embodiments, a hair graft or follicular unit may be implanted into the selected location simultaneously with making the site. In yet other embodiments, the methodology may be employed to simply provide a site making plan, which may later be implemented to provide actual implantation sites. Using hair transplantation as an example, the distance between the first and second implantation site locations may be determined from the density of follicular unit or hair grafts that is desired per unit area. For example, in a region of one square centimeter, one would typically desire a density of about 30-40 follicular units or hair grafts, a range of anywhere from 20 to 60 grafts in a one square centimeter region. This range will vary from patient to patient, and depend also upon the physician and the implantation procedure method adopted. From the desired density, an average required distance between follicular units or hair grafts can be determined. This value may be varied by the user and may be indicated, for example, via a user interface icon, which allows the user to increase or decrease the number of follicular units per unit measurement. Such a user interface icon is illustrated in FIG. 9.

Typically, implantation site making is initiated from a lower corner of the bound implantation region, defined by the boundary 720 or 730, so implantation sites 510 and 520 are located in the lower corner of the bound implantation region 720 or 730. During the site making process, often various fluids, including for example, blood and saline will be present on the body surface. It was discovered that it is advisable, especially in the computer-implemented or robotic hair transplantation procedures, that the harvesting or implantation process begin from the bottom of the frame, whether it be in the right or left corner. This way any appearing blood or other fluid will tend to flow downwards due to gravity, and therefore, will less likely compromise the image of the potential subsequent hair implantation sites, thus optimizing any image processing that may be implemented.

Returning back to the general methodology of FIG. 4a, assuming that there are at least two pre-existing or previously proposed sites (as described above) within the identified boundary, in step 420, a location for a candidate implantation site 530 is proposed or selected. The location of the candidate implantation site may be proposed, at least in part, based various parameters as explained in previously incorporated commonly assigned U.S. Patent Application Publication No. US 2013-0190776, for example, based on the desired density or a determined average distance between follicular units or hair grafts that can be derived from the desired density, in order to satisfy the density requirement. In some embodiments, proposing or selecting the location of the candidate implantation site may comprise only proposing its position relative to other sites or features, and the actual location that is the coordinates of the proposed candidate site may be determined in optional step 430. In other embodiments, proposing the candidate implantation site may be such that the coordinates have already been determined.

However, as explained in reference to FIGS. 1-3, such initially proposed procedure site of step 420 may not provide the best or desirable outcome. Therefore, in step 440, the locations of at least two pre-existing or previously proposed sites located, for example, within an examination region are determined. In reference to hair transplantation, pre-existing or previously proposed sites may include in different implementations any of the following: previously proposed sites, previously made sites, and/or implanted or pre-existing hair. Also, for the purposes of the present disclosure, the examination region is a region which is taken into consideration for determining locations of at least two pre-existing or previously proposed sites when proposing and verifying a location of a candidate implantation site. In other words, this region provides a limit on the size of an area which is considered and it may vary depending on a particular application. For example, with reference to hair transplantation, the examination region 540 may be based on the caliber and density of hair within an area. For example, a typical implantation distance between recipient sites ranges from 1.5 mm-2.0 mm. Therefore, the size of the examination region may be chosen to be a multiple of 2-4 of the typical implantation distance, for example, it could be represented by a generally circular area having a radius of approximately 3 mm to 8 mm, and more specifically about 5 mm to 6 mm. For example, in some embodiments, determination of the location of pre-existing or previously proposed sites within an examination region 540 may be an area within a 6 mm radius from the proposed candidate procedure site. This distance of 6 mm is such that one may expect to find 3 or 4 follicular units along a radius from the location of the proposed candidate procedure site to the edge of the region (a 6 mm span). The examination region may comprise a generally circular area or a segment thereof, with a radius equal to a multiple of implantation distance, though any shaped region may be utilized. Alternatively, or in addition, the examination region 540 may be based on other parameters. For example, implanting a hair too close to an existing hair may cause the existing hair to pop out, so there is typically a minimum distance between hairs that can be defined. The examination region 540 may, in this example, be based on this predefined distance, that is, a region around the proposed candidate procedure site which has a radius equal to a plurality of that predefined distance.

Figure 5B:
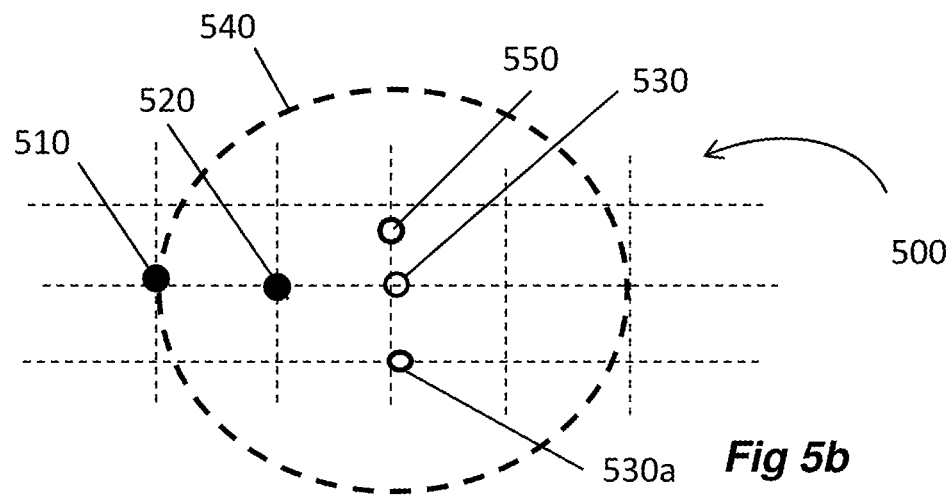

As indicated in FIG. 5b, the implantation sites identified as 510 and 520 can be seen to be within the examination region 540. Having determined these locations, in step 450, from the location or coordinate information, a processor may determine if these locations are such that together with a new proposed candidate site 530 they can be fit, for example, on a fitted (e.g., virtual) line, and/or form a predefined geometric shape. For the purposes of the current disclosure, a fitted line is a line that can be drawn through a set of points, and describes the trend of the points. For the purposes of the current disclosure, points which are located within a certain distance (e.g., up to 0.5 mm) on either side of a fitted line, that is, points that are offset up to 0.5 mm on either side of the fitted line, are considered to be positioned on the fitted line. It should be noted that 0.5.mm is used as an example only, and this value may vary depending upon application. Furthermore, a fitted line may be formed from points or coordinates in a 3-D environment. As a suitable approximation, 3D coordinates on a smooth surface (such as a scalp) may be projected on a 2D tangent plane to the scalp near a centroid of the 3D coordinates, and should it be possible to draw a fitted line through the points projected in the 2-D environment, the 3D coordinates would be considered to form a fitted line. A predefined geometric shape comprises known geometric shapes, such as and not limited to, triangles, rectangles, ovals or squares. Stating that the relevant points form a predefined geometric shape includes not only forming an exact predefined geometric shape but may also include some ranges of tolerances and errors, such that the resulting geometric shape is substantially close to the predefined geometric shape. Depending on a particular application, such range may include, for example, up to 0.5 mm. Various known techniques may be applied to acquire this information, and these techniques known to those skilled in the art so will not be described in detail here. Such techniques include, for example, a mathematical procedure for finding the best-fitting curve or line to a set of points, by minimizing the sum of squares of the offsets of the points from the curve or line, otherwise known as a least squares fitting approach. It will be appreciated that in some embodiments, the location of proposed candidate implantation sites, and the at least two pre-existing or previously proposed sites may comprise locations not only in a two dimensional coordinate system, but in a three dimensional coordinate system. In some embodiments, to ease calculation, the 3-dimensional coordinates of the locations may be projected into a 2-dimensional coordinate system and the determination made whether the points represent points on a virtual fitted line segment, and/or a predefined geometric shape, in the 2-dimensional coordinate system. In other embodiments, the 3-dimensional coordinates of the locations may be utilized to determine whether the points represent a predefined curve segment, if applicable.

If it is found in step 450 that the locations of the proposed candidate site 530 and the locations of the at least two pre-existing or the previously proposed sites 510 and 520, substantially form a fitted line and in some implementations optionally a predefined geometric shape, the initial proposed candidate site 530 will be rejected and instead another location for a candidate implantation site will be proposed. As seen in the example of FIG. 5b, the proposed candidate site 530 is positioned approximately on the same line with the pre-existing sites 510 and 520, and therefore, its location would be rejected or adjusted, as described by example below. In one shown implementation of FIG. 4a, the methodology returns to step 420 of the procedure, and one or more subsequent candidate implantation site(s), for example 550, may be proposed. The same process may be repeated as many times as needed. In some embodiments of the current disclosure, instead of proposing a brand new candidate site, the location of the original candidate implantation site 530 may be offset or adjusted (see step 425), for example, in a predetermined direction or in a predetermined radius. The processor may be configured such that is applies a predetermined offset, such as an offset of a predetermined distance shown by example in the y-direction in a negative, or downward direction, as illustrated by the adjusted candidate implantation site 530a on the next horizontal line of the grid 505. In an alternative example, the adjusted candidate implantation site 530a may be offset within a range of distances, or a band of distance, somewhere between the grid lines for example, in the positive y-direction, or in the downward direction. For example, the offset may be anywhere within the range up to 0.5 mm, but the range may depend on an implantation site density. Alternatively, the adjusted candidate implantation site may be proposed at a predetermined angle with respect to the initially proposed candidate site, or within a range of such angles. In addition the location of the candidate procedure site may be proposed based on one or more additional criteria, the additional criteria comprising criteria such as a minimum distance of travel from the procedure tool, and/or a criteria designed to improve one or more of speed, quality and efficacy of the procedure.

Figure 5C:
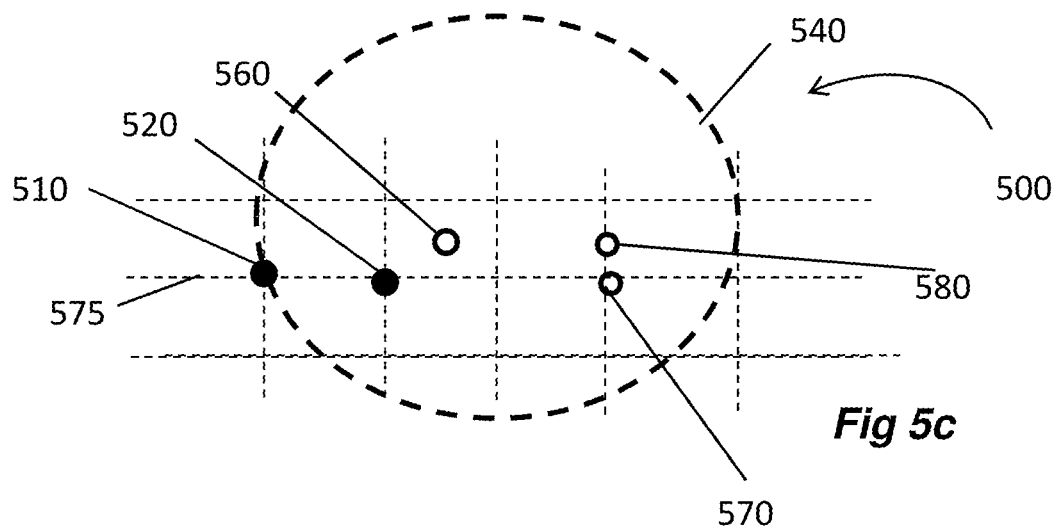

Having adjusted the original candidate site 530 or having proposed the new candidate implantation site, for example 560, the methodology is repeated as illustrated in FIG. 5c. Once again, the locations of at least two pre-existing or previously proposed sites are determined within an examination region 540. In this particular example, it can be seen that the implantation sites 510, 520 and 560 do not represent points on a substantially straight line segment. In addition, this particular example also satisfies an optional requirement that the location of the sites 510, 520 and 560 do not represent vertices of either an equilateral or an isosceles triangle, an example of a predefined geometric shape that must be avoided. Under these circumstances, according to step 470 of the methodology, the candidate proposed implantation site 560 can be confirmed and selected as an actual implantation site. Generally, in certain embodiments the analysis and/or logic may be provided to make sure that no at least three sites located within a defined examination region are positioned on a fitted line or form a predefined geometric shape or substantially close to such predefined shape.

The methodology can now be repeated, proposing a new candidate site and it is again determined if these location points substantially represent points on a fitted line or form a predefined geometric shape. In this example of FIG. 5c, the proposal of the candidate implantation site 570 in the examination region 540 is such that its location and the location of the implantation sites 510 and 520 represent points on a substantially straight line, as illustrated with respect to line 575 of the grid 505. Therefore, according to step 460 of the methodology, another candidate implantation site is proposed. In this instance, the next site proposed, site 580, is offset from that of the proposed candidate implantation site 570. This offset location being such that the location of the implantation sites 580, 510 and 520 no longer represent points on a fitted line. In addition, they also do not represent points on or form a predefined geometric shape (such as a square, or rectangle, or equilateral or isosceles triangle). The procedure comprising the step of proposing a location of a new candidate procedure site can be repeated until a desired number of sites have been proposed in a certain area, such as within the boundary 720,730 which defines a recipient region on a body surface of a patient, or such that a desired density has been reached. In some instances, it may not be possible to reach the desired density or number of sites, but the process may be repeated until the location of as many follicular units implantation sites as possible may be proposed, according to the methodology applied.

In this manner, multiple implantation sites can be selected, into which follicular units or hair grafts can be implanted, such that a randomized (e.g., in a controlled manner) distribution of follicular units or hair grafts can be achieved. The randomized distribution described in the present disclosure enables an improved natural looking distribution to be attained. As discussed above, additionally, the selection of the predetermined region 540 enable the user to specify the density of follicular units or hair grafts to be implanted into any recipient region. The result is illustrated in FIG. 6a, in which the randomized implantation site locations can be seen, the implantation locations being distributed across the bald region 600, such that the location of the implantation sites do not represent points on a fitted line, or form a predefined geometric shape, or both, if such fitted line or predefined geometric shape were to be drawn through the implantation site locations. In another example, a further method of determining a location of a procedure site is provided. The method comprises determining locations of at least two pre-existing or previously proposed sites and using a processor to propose a location of a new candidate procedure site such that the proposed location of the new candidate procedure site and the at least two pre-existing or previously proposed sites do not represent points on a fitted line or a form a predefined geometric shape, if the fitted line or predefined geometric shape were to be drawn through the locations of the sites. In this methodology, locations of two or more pre-existing or previously proposed sites are determined. A new candidate procedure site is then proposed based on the locations of the two or more pre-existing or previously proposed sites, such that when placed at its location, the new candidate procedure site does not form a fitted line or the predefined geometric shape were to be drawn through the locations of the sites.

The general methodology of FIG. 4a may be modified and adjusted in various embodiments, for example, to provide additional solutions and to address certain issues that may be encountered in various implementations. For example, in reference to hair transplantation, one challenge in creating incisions or implantation sites is where to place them with respect to existing hair. Generally, the incision sites should not be too close to existing terminal (healthy) hair follicles, as placement too close to terminal follicles may increase the chance of loss of the healthy terminal hair due to shock. At the same time, incision sites may be placed next to non-terminal hair, such as vellus hair, dying, miniaturized, or non-regenerating hair, as these types of hair are deemed unrecoverable, an effect associated with male pattern baldness.

Classification of terminal and non-terminal hair (such as vellus hair) additionally provides a means by which a physician, or an image guided system may adjust the proposed procedure site based on the number of terminal or healthy hairs that are present in the region accordingly. In this manner, the physician or such image guided system may choose to compensate for the inclusion of these terminal hairs, and not make additional implantation procedure sites which would interfere or compromise the integrity of these terminal hairs. In addition, it would allow the physician or such image guided system to take into consideration any non-terminal hair, such as vellus hair, which would eventually fall-out or disappear anyway and will not aid in the overall look achieved once the hair implantation procedure had been performed.

Figure 4B:
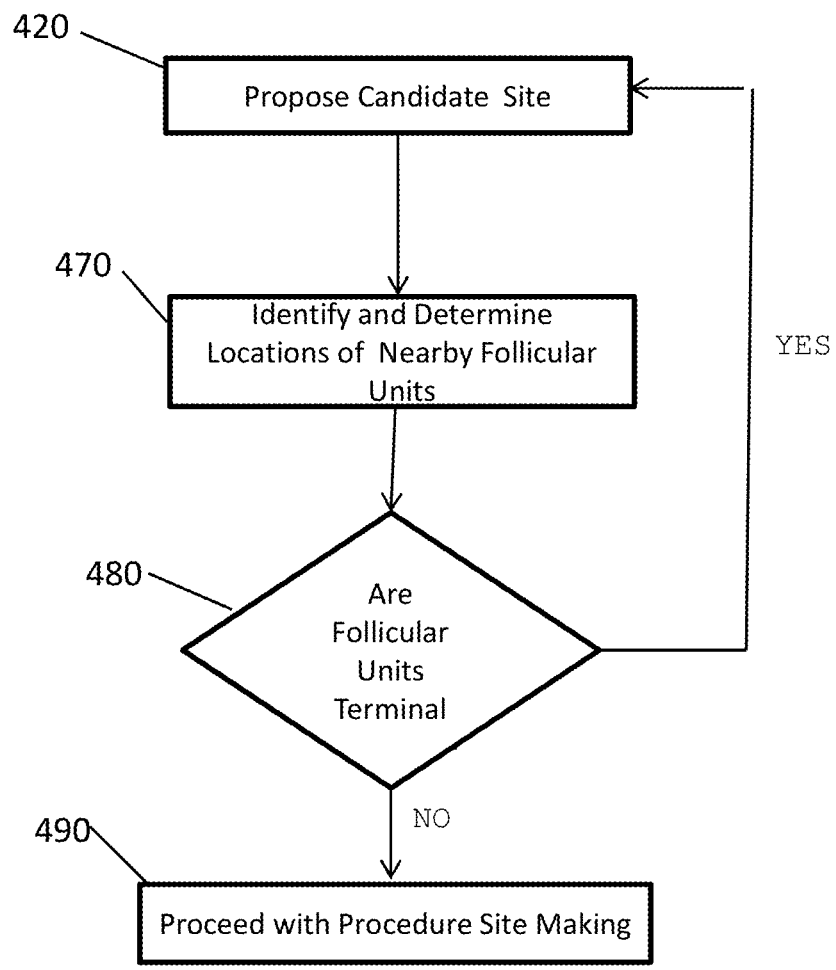
FIG. 4b is a flow chart illustrating an example of a general methodology for accounting for terminal hair.

FIG. 4b is a flow chart illustrating an example of a general methodology employed by the present disclosure that may, if desirable, account for any existing terminal or non-terminal hair in the relevant region. Once a candidate site has been proposed in step 420, it is determined whether any hair exists nearby, for example, within a certain distance from the candidate site. A list of such nearby existing hair may be created. The above-mentioned distance for determining location of the existing hair may be in a range, for example, of up to 2 mm from the location of the proposed candidate procedure site, however this number will vary depending on a hair density. Having identified these neighborhood follicular units, in step 480, a determination is made as to whether the identified follicular units comprise terminal hairs, or if they are in non-terminal hairs.

Figure 10:
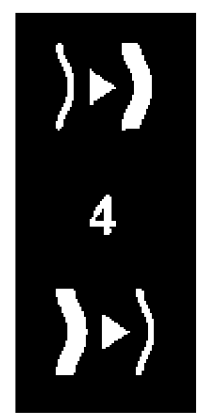
FIG. 10 illustrates an example of a user interface icon, which may be utilized to vary the caliber of terminal or non-terminal hairs, according to another embodiment.

In one embodiment of the current disclosure, the classification of follicles as non-terminal may comprise determining one or more, or a combination, of the properties described below. Such determination may be carried out by means of image processing. Non-terminal hair typically has a caliber of less than 35 μm or less than 0.05 mm, are lighter in color with respect to terminal hair on the same patient, and are generally shorter than terminal hair, for example, the average length of a vellus hair ranging from 0.5-1.0 mm. By determining and analyzing, for example, by means of imaging processing, one or more of these properties, one is able to classify the identified follicular units as either terminal or non-terminal hair accordingly. For example, to improve correct classification of the hair as terminal or non-terminal, a scoring system may be employed that gives certain weight to each of the above properties (e.g., caliber, color, lengths, etc.) and based on the weighted combined score the analyzed hair may be determined as terminal or non-terminal. It will be apparent however, that the caliber of terminal or non-terminal hair may vary from patient to patient. Therefore, according to another aspect of the disclosure, the user may take this into consideration and vary the value associated with a threshold considered for a particular patient to differentiate terminal and non-terminal hair. For example, if a patient has very light hair, then non-terminal hair may be almost translucent, or on a patient with very thick hair, a non-terminal hair may be thicker than the average thickness of other patients' non-terminal hair. Such variations may be implemented via a user interface icon, such as that illustrated in FIG. 10. In addition, the identification of terminal hairs may be highlighted for the user, by means of a colored graphical depiction on the screen.

As indicated earlier, ensuring that a candidate implantation site is not proposed at a location which is too close to a healthy terminal hair reduces the chance of loss of the healthy terminal hair due to shock. However, should the existing follicular unit comprise vellus hair, dying hair, miniaturized or non-regenerating hair, that is hair that is typically short, fine, light-colored and barely noticeable, it may be acceptable to propose a candidate implantation site close to such a hair. Therefore, should it be determined as a result of step 480 that the identified hair comprises a non-terminal hair, for example a vellus hair, a decision may be made to simply disregard such non-terminal hair and proceed with a regular logic of the procedure site making methodology, such as that described with reference to FIG. 4*a*. The identified non-terminal hair will not be considered a pre-existing site for the purposes of step 440, and the methodology will proceed accordingly. The described evaluation enables, for example, the processing system or the physician, to determine that a particular hair should or should not be considered before determining if its location represents a point of a substantial straight line, predefined curve segment or predefined geometric shape.

On the other hand, if as a result of step 480 it is determined that the identified follicular unit comprises a terminal hair, it may be necessary to consider proposing another candidate procedure site. Therefore, the methodology may be used to ensure that the candidate implantation site is not selected at a location which is too close to a healthy terminal hair, and thus reducing the chance of loss of the healthy terminal hair due to shock.

Figure 8A:
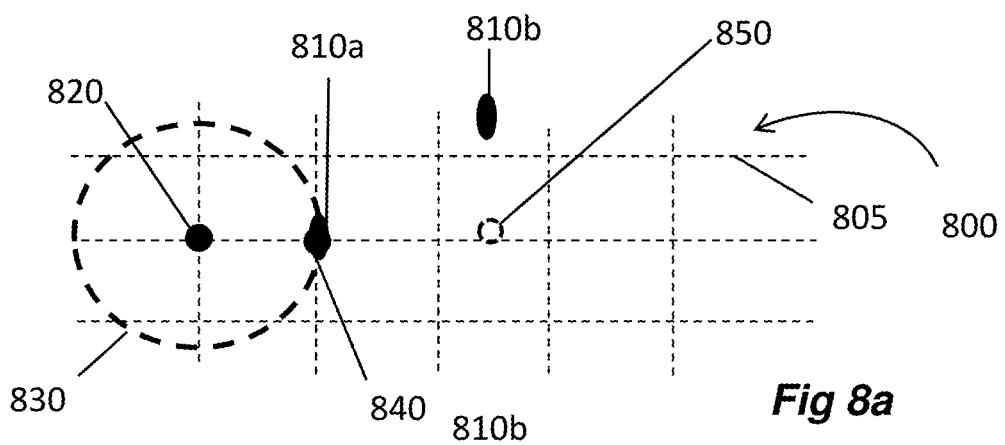
FIGS. 8a and 8b show various examples of implementations of the methodology according to another embodiment of the present disclosure.

Turning now to FIG. 8*a*, in this example, the identification of terminal hairs according to the methodology depicted in FIG. 4*b* has additionally been incorporated into the methodology for proposing candidate procedure sites as depicted in FIG. 4*a*. Here, the implantation region portion 800 comprises a bald region with the pre-existing follicular units 810*a* and 810*b*. It should be noted that although these sites are not implantation sites but rather pre-existing hair, for the purposes of the present disclosure, these pre-existing follicular units 810*a* and 810*b* are considered a pre-existing sites, and as such, are taken into consideration when proposing a candidate implantation site in step 420.

In step 420 of the methodology, a candidate implantation site 840 is proposed at a predetermined minimum distance from a previously proposed implantation site 820 such that a desired implantation density can be achieved, but far enough away from the previously proposed implantation site 820 such that the integrity of any follicular unit eventually implanted into site 820 will not be compromised.

In some embodiments, if desired, an identification of nearby or neighboring follicular units in the examination region may independently be carried out, as identified in step 470 of FIG. 4*b*, this identification may comprise identifying any hair within an examination region and also, for example, if it is within a predetermined minimum distance 830 from the proposed candidate site. Such minimum distance may be, for example, in a range of 1 mm to 2 mm and depend on the desired density of hair in the area. Having determined in step 480 that existing follicular unit 810*a* of FIG. 8*a* is a terminal hair, it is therefore not recommended that an implantation site be created at 840, as doing so would be detrimental to the healthy hair 810*a* which is positioned approximately at the same location as the proposed site 840, as can be seen in FIG. 8*a*. Consequently, the methodology rejects the proposed site 840 and instead returns to the step 420 to propose another candidate implantation site 850. Having proposed this subsequent candidate implantation site 850, the methodology of FIGS. 4*a* and 4*b* is again followed. The classification of terminal and non-terminal (vellus or miniaturized hair) additionally provides a means by which terminal or healthy hairs can be included to form part of the density of hairs in the recipient region, and non-terminal hairs can be excluded in the calculation of the density of hair in the recipient region. It will be appreciated that recipient areas with a higher number of terminal follicles or hair will require less implantation sites than recipient areas with a higher number of non-terminal hair.

Figure 8B:
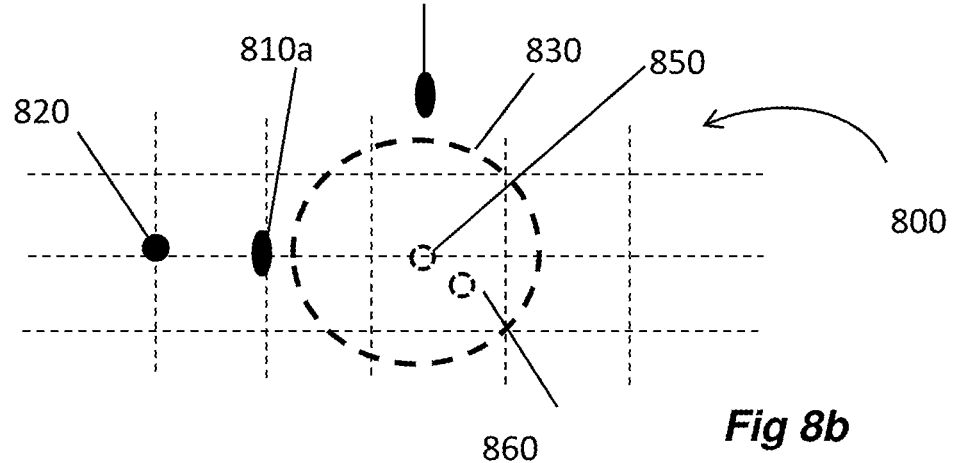

In examining the proposed candidate implantation site 850 according to the methodology of FIGS. 4*a* and 4*b*, it is confirmed in step 480 that both hair 810*a* and 810*b* are terminal and that they are both far enough from the proposed site 850 not to cause any damage if a new site is created at the location 850. However, the proposed site 850 will still be rejected by performing step 450 of the methodology of FIG. 4*a* because, as can be seen in FIG. 8*a*, the proposed implantation location 850 and the locations of the two existing follicular units 810*a* and 810*b* represent the vertices or form an isosceles triangle. Therefore, as shown in FIG. 8*b*, another candidate implantation site 860 is proposed. In this embodiment, the candidate site 860 is not a brand new proposed site but it rather represents an offset from the location of the previously proposed site 850 such that its location does not represent points on a fitted line or forms a predefined geometric with the locations of existing follicular units 810*a* and 810*b*. Having offset the location of the proposed candidate procedure site, steps 440 and 450 of FIG. 4*a* are repeated and a determination is made if the locations of the proposed implantation location 860, and the locations of the two existing follicular units 810*a* and 810*b* represent points on a fitted line or form a predefined geometric shape. In this particular instance, the sites 810*a*, 810*b* and 860 do not represent points on a fitted line and they do not form a predefined geometric shape, therefore, the proposed site location can be now confirmed (step 460).

In this manner multiple implantation sites can be selected, into which follicular units or hair grafts can be implanted, such that a randomized distribution of follicular units or hair grafts can be achieved. The randomized distribution still enabling a more uniform distribution to be attained than that illustrated in FIGS. 1-3 above. Once again, the selection of the distance enables the user to specify the density of follicular units or hair grafts to be implanted into any recipient region. The result is illustrated in FIG. 6b, in which the randomized implantation site locations can be seen, the implantation locations 610 (shown as black circles) being distributed across the bald region 650, and among the existing follicular unit sites 620 (shown as black squares).

In order to provide a more natural-looking appearance, in some embodiments of the current disclosure, an additional randomness may be specified when proposing a candidate site, for example as 0.5 mm, this additional randomness may be an absolute value or may provide a range in distance which the additional randomness may comprise. Furthermore, this additional randomness may be in a specific direction, or a random direction, or in multiple directions. In other words, each follicular unit location may additionally be perturbed by 0.5 mm randomly and the resulting locations are used, rather than the proposed location.

In yet another embodiment of the current disclosure, an implantation site making methodology as described in commonly assigned U.S. Patent Application Publication No. US 2013-0190776 may additionally be applied. For example, the boundary 710 or 720 which defines the recipient region may be imaged and the image may have a virtual grid superimposed within the boundary 710 or 720, the grid comprising a network of uniformly spaced horizontal and perpendicular lines, providing for potential or candidate locations at nodes of the grid, within the boundary. In this embodiment, the next proposed candidate implantation site may be proposed in one direction, for example, traveling to the right, along a particular grid row, from one node to another. If it is found that an implantation site should not be created at that particular location, or node, the next proposed candidate implantation site would be proposed traveling horizontally, in the same direction, to the next node to the right, and so on. Once the length of the horizontal line within the boundary had been traversed, and the vertical boundary reached, the system would propose the next implantation site on the next row, incrementing the row number, and either traveling along with subsequent row from right to left, or left to right. In this manner, close packing or a high density of implantation sites may be achieved, by placing the horizontal and vertical grid lines as close as possible. In various embodiments, "exclusion zones" around the procedure sites may be implemented as described in the above-mentioned U.S. Patent Application Publication No. US 2013-0190776. An exclusion zone is a region within which is not desirable to perform a procedure or operation, for example, the region from which harvesting follicular units or into which implantation of the follicular units is not desirable. In some embodiments, the exclusion zone may be defined as a closed polygon, for example, a polygon of substantially tear-drop shape on a surface of the body, or for example a donor area, such as scalp. The exclusion zone may be based on various criteria, including, for example, avoiding problems such as the potential implant site coinciding, intersecting with or coming too close to an already existing harvesting/implanting sites or existing hair, or merely defining the minimum separation of follicular units to be implanted for medical or aesthetic reasons. In addition, some embodiments may comprise different methods for selecting follicular unit harvesting or implantation sites in order to closely pack such follicular unit harvesting or implanting sites. Methods such as the "lowest and closest" method, an "overlap priority" method, a "position priority" method, a "pattern-based" method, and/or a combination of these methods.

Figure 11:
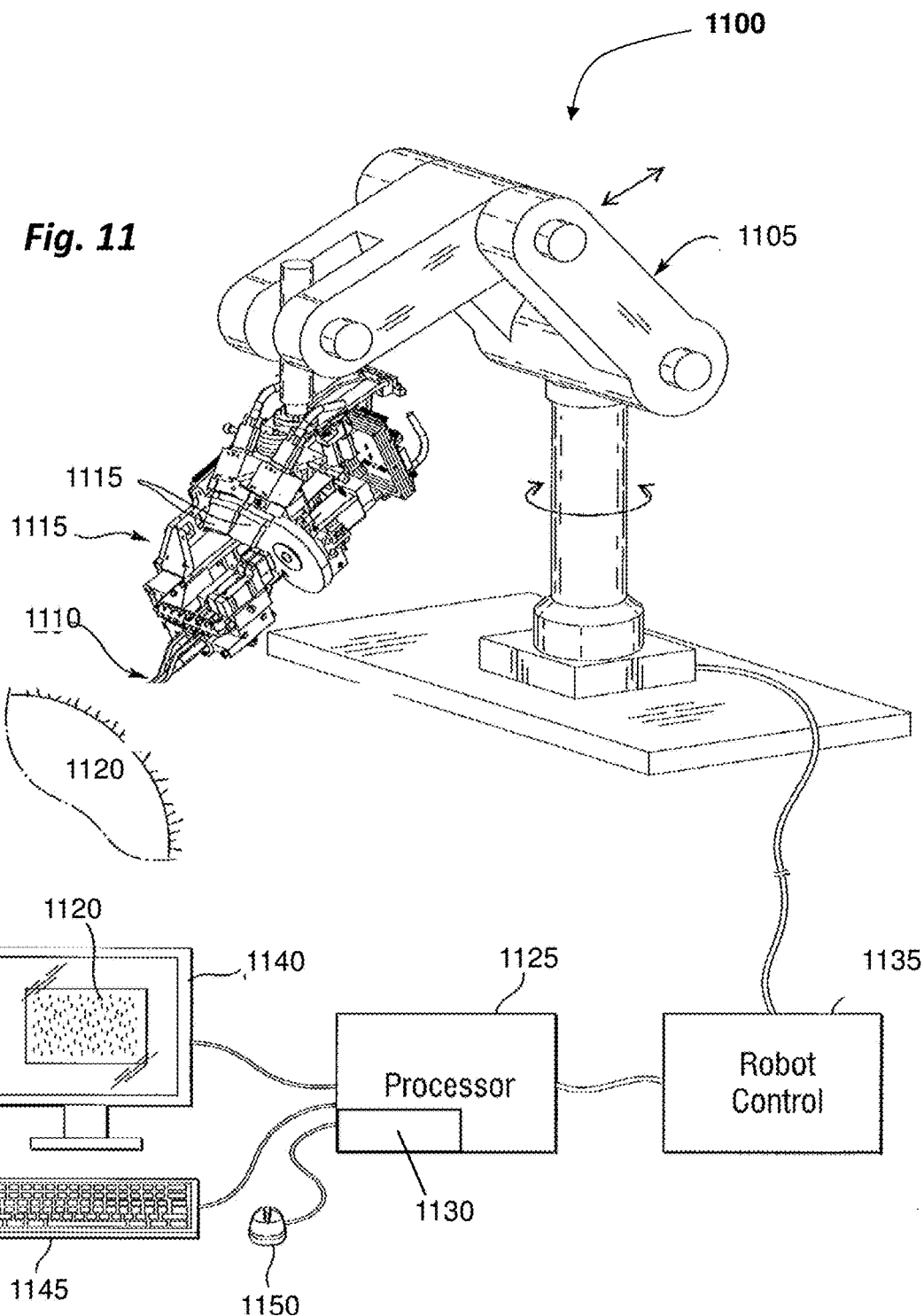
FIG. 11 is a schematic representation of an example of a robotic system that could be used in various embodiments of the present disclosure.

An example of a system that may be used with the present invention is schematically shown in FIG. 11. FIG. 11 is a schematic perspective view of an example of a robotic system 1100 that may be used for performing various procedures, such as making incisions, creating implantation sites (including without limitation, may be used for hair implantation and/or harvesting). The system 1100 includes a robotic arm 1105 to which is coupled a tool 1110. Various motors and other movement devices may be incorporated to enable fine movements of an operating tip of the tool 1110 in multiple directions. The robotic system 1100 further includes at least one image acquisition device 1115, which is described in more detail below. The image acquisition device may be mounted in a fixed position, or it may be coupled (directly or indirectly) to a robotic arm 1105 or other controllable motion device. The operating tip of the tool 1110 is shown positioned over a body surface 1120, in this case a part of the patient scalp having hair follicles thereon. In some embodiments, an image acquisition device may be provided separately and not included in the system. In those embodiments, an interface may be provided that allows various other components or modules of the system, such as image processing component, to interact with the separate image acquisition device.

One or more processor 1125 of FIG. 11 may comprise an image processor 1130 for processing images obtained from the image acquisition device 1115. The image processor 1130 may be a separate device or it may be incorporated as a part of the processor 1125. One of the processors 1125 may also instruct the various movements of the robotic arm 1105, including the tool 1110 that may be operatively connected to the robotic arm. The processor 1125 may act, for example, through a controller 1135 as schematically shown in FIG. 11. The controller 1135 may be operatively coupled to the robotic arm and configured to control the motion of the robotic arm, including the motion based on the images or data acquired by the image acquisition device. Alternatively, controller 1135 may be incorporated as a part of the processor 1125, so that all processing and controls of all movements of all the tools, the robotic arm and any other moveable parts of the assembly, including those based on the images or data acquired by the image acquisition device, are concentrated in one place. The system 1100 may further comprise a monitor 1140, keyboard 1145, and mouse 1150. In addition or alternatively, various parameters and actions may be input via a remote input device, or selection may be provided by drop-down menus or an automated algorithm or similar such means and user interfaces. For example tablets or mobile devices, which allow touch screen commands and gestures to be recognized via stylus, pen or finger(s). A magnified image of the body surface 1120 can be seen on the monitor 1140. In addition, the system 1100 may comprise other tools, devices and components, for example, those useful in harvesting, and/or implantation of the hair follicles, or in hair treatment planning, or other procedures. The system further comprises an interface adapted to receive an image data, various parts of the system allow an operator to monitor conditions and provide instructions, as needed. The processor 1125 may interact with the imaging device 1115 via the interface (not shown). The interface may include hardware ports, cables, leads, and other data transmission means, or it may comprise a computer program.

Some non-limiting examples of an image acquisition device 1115 shown in FIG. 11 include one or more cameras, such as any commercially available cameras. Of course, various image capture devices (or imaging devices) could be used with any of the embodiments of the systems and methods described herein. For example, the imaging device may be one or more cameras, such as any commercially available cameras, including those used in the mobile phones, tablets, depth cameras. While stereo or multi-view imaging devices are very useful in the present invention, it is not necessary to employ such geometries or configurations, and the present invention is not so limited. Likewise, although it is preferred that the image acquisition device be a digital device, it is not necessary. For example, the image acquisition device could be an analog TV camera that acquires an initial image which is then processed into a digital image (for example, via an analog-to-digital device like a commercial-off-the-shelf frame grabber) for further use in the method of the present invention. The image acquisition device may be coupled to a processing system, shown incorporated in the processor 1125 in FIG. 11, to control the imaging operation and process image data. One or more processors for use with the present disclosure may comprise any suitable device programmed and configured to perform various methods described in detail in the present disclosure, including methods directed to automated proposal and selection of follicular unit implantation sites. For example, the processor or other computing device for use in the present disclosure may be one or more processors comprising a set of instructions for executing operations, the set of instructions including instructions for processing one or more images of a body surface to determine locations of a plurality of distinctive fiducials appearing in the one or more images which may define a boundary in those embodiments where the boundary is determined. The set of instructions may comprise determining locations of a proposed procedure site and at least two pre-existing or previously proposed sites within an examination region; determining if these locations form a fitted line with respect to each other; and if the location of the proposed procedure site and the location of the at least two pre-existing or previously proposed sites form a fitted line, adjusting the location of the proposed procedure site such that it does not form such fitted line. The set of instructions may also comprise instructions for placing a tool at the adjusted location of the proposed procedure site to perform a procedure. One or more processors may be programmed to perform various steps and methods as described in references to various embodiments and implementations of the present disclosure. It will be understood by those of ordinary skill in the art that the image processor for use with the present disclosure may be programmed and configured to perform various known image processing techniques, for example, segmentation, edge detection, object recognition and selection. These techniques are generally known and do not need to be separately described here.

By way of example, and not limitation, a suitable processor or image processor may be a digital processing system, which includes one or more processors or other type of device. For example, a processor (image processor) may be a controller or any type of personal computer ("PC"). Alternatively, the processor (image processor) may comprise an Application Specific Integrated Circuit (ASIC) or Field Programmable Gate Array (FPGA). The processor may also include memory, storage devices, and other components generally known in the art and, therefore, they do not need to be described in detail here. The above-described processor could be used in conjunction with various partially automated and fully automated (including robotic) hair transplantation and treatment systems and devices, including but not limited to systems for hair harvesting, or hair transplantation.

Embodiments of the systems of the present disclosure may be comprised of various modules, for example, as discussed below. Each of the modules can comprise various sub-routines, procedures and macros. Each of the modules may be separately compiled and linked into a single executable program. In light of the above, the description of each of the modules is used for convenience of the description of functionality only. In one embodiment, the one or more processing units may comprise one or more modules to determine the location of a proposed candidate procedure site and at least two other sites within an examination region. Additionally, a module may determine if the location of the proposed candidate procedure site and the at least two other sites would substantially represent points on a fitted line or form a predefined geometric shape if such fitted line or geometric shape were to be drawn through the locations of the sites. Another module may determine a necessary offset to be applied to the location of the proposed candidate procedure site.

Any process descriptions, elements or blocks in the flow diagrams described herein and/or depicted in the attached figures should be understood as potentially representing modules, segments, or portions of code which include one or more executable instructions for implementing specific logical functions or elements in the process. Further, the functions described in one or more examples may be implemented in hardware, software, firmware, or any combination of the above. If implemented in software, the functions may be transmitted or stored on as one or more instructions or code on a computer-readable medium, these instructions may be executed by a hardware-based processing unit, such as one or more processors, including general purpose microprocessors, application specific integrated circuits, field programmable logic arrays, or other logic circuitry.

The foregoing illustrated and described embodiments of the disclosure are susceptible to various modifications and alternative forms, and it should be understood that the applications as generally disclosed herein, as well as the specific embodiments described herein, are not limited to the particular forms or methods disclosed, and that many other embodiments are possible within the spirit and the scope of the present disclosure. Moreover, although individual features of one embodiment may be discussed herein or shown in the drawings of the one embodiment and not in other embodiments, it should be apparent that individual features of one embodiment may be combined with one or more features of another embodiment or features from a plurality of embodiments. By way of non-limiting example, it will be appreciated by those skilled in the art that particular features or characteristics described in reference to one figure or embodiment may be combined as suitable with features or characteristics described in another figure or embodiment. Applicant regards the subject matter of the disclosure to include all novel and nonobvious combinations and sub-combinations of the various steps, elements, features, functions, and/or properties disclosed herein. Furthermore, the methodologies described can be applied to any treatment, and is not limited to hair transplantation.

In the Detailed Description, reference is made to the accompanying drawings that show by way of illustration some examples of embodiments in which the invention may be practiced. In this regard, directional terminology, such as "right", "left", "front", "side", and "top", etc., are used with reference to the orientation of the Figure(s) being described.

Because components or embodiments of the present invention can be positioned or operated in a number of different orientations, the directional terminology is used for purposes of illustration and is in no way limiting.

It will be further appreciated by those skilled in the art that the current disclosure is not limited to the use of a particular system, and that automated (including robotic), semi-automated, and manual systems and apparatus may be used for positioning and actuating the respective tools and other devices and components disclosed herein.

While the current disclosure has been described in its preferred embodiments, it is to be understood that the words which have been used are words of description and not of limitation. Therefore, changes may be made within the appended claims without departing from the true scope of the disclosure.

What is claimed is:

1. A method for automatically selecting a location of a procedure site on a patient, the method comprising:
   proposing a candidate procedure site on a patient;
   identifying a follicular unit that exists within a certain distance from the candidate procedure site;
   automatically determining, using image processing, if the existing follicular unit is terminal or non-terminal; and
   selecting from available options of:
   1) if the existing follicular unit is determined to be non-terminal, proceeding with procedure site making at the proposed candidate procedure site; and
   2) if the existing follicular unit is determined to be terminal, proposing another candidate procedure site such that the candidate procedure site is not too close to the existing follicular unit.

2. The method of claim 1, wherein a non-terminal follicular unit is a vellus follicular nit, a dying follicular unit, or a non-regenerating follicular unit.

3. The method of claim 1, wherein proposing another candidate procedure site such that the candidate procedure site is not too close to the existing follicular unit comprises offsetting the location of the candidate procedure site in one or more predetermined directions.

4. The method of claim 1, wherein proposing another candidate procedure site such that the candidate procedure site is not too close to the existing follicular unit comprises offsetting the location of the proposed candidate procedure site by a predetermined distance.

5. The method of claim 1, wherein the proposed candidate procedure site comprises a follicular unit implantation site.

6. The method of claim 1, wherein identifying a follicular unit that exists within a certain distance from the candidate procedure site comprises identifying a follicular unit that exists within 2 millimeters from the candidate procedure site.

7. A method of selecting a location of a procedure site, the method comprising:
   proposing a candidate procedure site on a patient;
   identifying a follicular unit that exists within a certain distance from the candidate procedure site;
   automatically classifying, using image processing, the existing follicular unit as terminal or non-terminal; and
   selecting from available options of:
   1) if the existing follicular unit is classified as non-terminal, proceeding with procedure site making at the proposed candidate procedure site; and
   2) if the existing follicular unit is classified as terminal, proposing another candidate procedure site such that the candidate procedure site is not too close to the existing follicular unit.

8. The method of claim 7, wherein a non-terminal follicular unit is a vellus follicular nit, a dying follicular unit, or a non-regenerating follicular unit.

9. The method of claim 7, wherein proposing another candidate procedure site such that the candidate procedure site is not too close to the existing follicular unit comprises offsetting the location of the candidate procedure site in one or more predetermined directions.

10. The method of claim 7, wherein proposing another candidate procedure site such that the candidate procedure site is not too close to the existing follicular unit comprises offsetting the location of the proposed candidate procedure site by a predetermined distance.

11. The method of claim 7, wherein the proposed candidate procedure site comprises a follicular unit implantation site.

12. The method of claim 7, wherein identifying a follicular unit that exists within a certain distance from the candidate procedure site comprises identifying a follicular unit that exists within 2 millimeters from the candidate procedure site.

13. A system for selecting a location of a procedure site, the system comprising:
   a user interface including a user input device;
   at least one non-transitory storage medium storing instructions, and
   one or more modules for executing operations on image data, the one or more modules comprising instructions for:
      proposing a candidate procedure site on a patient;
      identifying a follicular unit that exists within a certain distance from the candidate procedure site;
      automatically determining, using image processing, if the existing follicular unit is terminal or non-terminal; and
      selecting from available options of:
      1) if the existing follicular unit is determined to be non-terminal, proceeding with procedure site making at the proposed candidate procedure site; and
      2) if the existing follicular unit is determined to be terminal, proposing another candidate procedure site such that the candidate procedure site is not too close to the existing follicular unit.

14. The system of claim 13, wherein a non-terminal follicular unit is a vellus follicular nit, a dying follicular unit, or a non-regenerating follicular unit.

15. The system of claim 13, wherein proposing another candidate procedure site such that the candidate procedure site is not too close to the existing follicular unit comprises offsetting the location of the candidate procedure site in one or more predetermined directions.

16. The system of claim 13, wherein proposing another candidate procedure site such that the candidate procedure site is not too close to the existing follicular unit comprises offsetting the location of the proposed candidate procedure site by a predetermined distance.

17. The system of claim 13, wherein the proposed candidate procedure site comprises a follicular unit implantation site.

18. The system of claim 13, wherein identifying a follicular unit that exists within a certain distance from the candidate procedure site comprises identifying a follicular unit that exists within 2 millimeters from the candidate procedure site.

* * * * *